United States Patent [19]

Dutra et al.

[11] 4,322,238

[45] Mar. 30, 1982

[54] N-NITROSO-N-PHOSPHONOMETHYL-GLYCINONITRILE ESTERS AND THE HERBICIDAL USE THEREOF

[75] Inventors: Gerard A. Dutra, Ladue, Mo.; James A. Sikorski, West Lafayette, Ind.

[73] Assignee: Monsanto Company, St. Louis, Mo.

[21] Appl. No.: 177,653

[22] Filed: Aug. 13, 1980

[51] Int. Cl.³ .......................... A01N 57/18; C07F 9/40
[52] U.S. Cl. ........................................ 71/86; 260/923; 260/940
[58] Field of Search ..................... 260/923, 940; 71/86

[56] References Cited

U.S. PATENT DOCUMENTS

| | | | |
|---|---|---|---|
| 3,888,915 | 6/1975 | Alt | 71/86 |
| 4,025,331 | 5/1977 | Leber | 71/86 |
| 4,067,719 | 1/1978 | Dutra | 71/86 |
| 4,120,689 | 10/1978 | Dutra | 71/86 |

*Primary Examiner*—Anton H. Sutto
*Attorney, Agent, or Firm*—Gordon F. Sieckmann; Howard C. Stanley

[57] ABSTRACT

This disclosure relates to N-nitroso-N-phosphonomethylglycinonitrile compounds, the preparation thereof and their use as herbicides and in herbicidal compositions.

18 Claims, No Drawings

N-NITROSO-N-PHOSPHONOMETHYL-GLYCINONITRILE ESTERS AND THE HERBICIDAL USE THEREOF

This invention relates to N-nitroso-N-phosphonomethylglycinonitrile compounds, the preparation thereof and their use as herbicides and in herbicidal compositions.

The N-nitroso-N-phosphonomethylglycinonitrile compounds of this invention are those having the formula

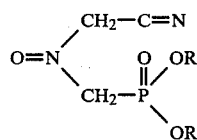

wherein R is a member of the group consisting of hydrogen, phenyl and phenyl substituted with from 1 to 2 substituents selected from the class consisting of halogen, loer alkyl and lower alkoxy.

The terms "lower alkyl" and "lower alkoxy" as employed herein refer to those alkyl and alkoxy derivatives containing from 1 to 4 carbon atoms, for example, methyl, ethyl, propyl, isopropyl, butyl, methoxy, ethoxy, isopropoxy, isobutoxy and the like.

The compounds of the instant invention are produced by the reaction of an N-phosphonomethylglycinonitrile compound with a nitrite salt in the presence of a hydrohalic acid. For example, N-nitroso-N-(diphenoxy)phosphonomethylglycinonitrile is produced by reacting approximately equal molar quantities of sodium nitrite with N-(diphenoxy)phosphonomethylglycinonitrile in an aqueous suspension in the presence of hydrochloric acid at a temperature of from $-5°$ C. to about 25° C. and preferably at about 0° to b 5° C. Nitrites which can be employed in the process of this invention include the alkali metal and alkaline earth metal nitrites.

In conducting the process of the instant invention, the ratio of the alkali metal nitrite to the N-phosphonomethylglycinonitrile compound is not narrowly critical and can be varied over a wide range, i.e., from about 1:10 to 10:1 molar ratios. Of course, it is preferred to employ the alkali metal nitrite and the N-phosphonomethylglycinonitrile compound in approximately equal molar amounts, i.e., molar ratio of from about 1.05:1 to 1:1.05 inasmuch as a large excess of one over the other renders a separation of the product more difficult.

The temperature at which the process is conducted can vary from about $-5°$ C. to about 25° C. It is preferred for convenience to conduct the process at a temperature of from about $-5°$ C. to 25° C.

The compounds and compositions of the present invention find use as herbicides.

The following examples serve to further illustrate the invention. All parts are parts by weight unless otherwise expressly set forth.

EXAMPLE 1

Diphenoxyphosphinylmethylglycinonitrile (3.02 g, 0.001 mole) and water (30 ml.) were charged into a 100 ml. 3-necked flask equipped with overhead stirrer and stirred to yield a slurry. The slurry was cooled to 0° C. and 2.5 ml. of 10-normal hydrochloric acid was added. Sodium nitrite (0.77 g) dissolved in 10 ml. of water was added dropwise at such a rate that the temperature did not exceed 5° C. The resulting heterogeneous mixture was stirred at room temperature for 2.5 hours yielding a white solid. The white solid was collected by filtration, washed with water and air-dried to yield (N-nitroso-N-cyanomethylamino)methylphosphonic acid, diphenyl ester, m.p. 76°–78° C., hving the following analysis:
Calculated: C, 54.38; H, 4.23; N, 12.69.
Found: C, 54.17; H, 4.22; N, 12.61.

EXAMPLE 2

Di(3-methyl-4-chlorophenoxy)phosphinylmethylglycinonitrile (10 g, 0.003 mole), water (150 ml.) and 15 ml. of 10-normal hydrochloric acid was charged into a reaction flask and cooled to 0° C. While maintaining the temperature below 0° C., 3.45 g of sodium nitrite dissolved in 25 ml. of water was added. The reaction mixture was stirred at 0° C. for 1 hour and then at room temperature for 1 hour until all of the red-orange oil had disappeared to yield a yellow semi-solid that adhered to the sides of the flask. The water was decanted from the yellow semi-solid. The yellow semi-solid was dissolved in methylene chloride, dried and concentrated to yield a yellow oil (11.0 g). Nuclear magnetic resonance spectral analysis indicated that the reaction was incomplete. The reaction mixture was stored at room temperature for several months. The resulting yellow oil (9.72 g) was dissolved in chloroform and filtered to remove approximately 1 g of the yellow solid. The remainder solution was adhered to 17 g of silica gel and subjected to high pressure liquid chromatography employing a 70% cyclohexane:30% ethyl acetate mixture. Fractions 9–13 were combined to obtain 2.3 g of yellow oil which contained some phenol. The yellow oil was dissolved in methylene chloride, washed with cold 5% sodium hydroxide solution three times and then with cold water two times. The methylene chloride solution was then dried and concentrated to obtain alpha-[N-(cyanomethyl)-N-nitrosoamino]methylphosphonic acid, di(4-chloro-3-methylphenyl) ester, as a light yellow oil (1.5 g) ($n_D^{25}$ 1.5653) having the following analysis:
Calculated: C, 47.68; H, 3.77; N, 9.81.
Found: C, 47.93; H, 3.82; N, 9.71.

EXAMPLE 3

Di(2-methoxyphenoxy)phosphinylmethylglycinonitrile methane sulfonic acid salt (9.16 g, 0.02 mole) and 15 ml. of 10-normal hydrochloric acid were combined in 150 ml. of water. The resulting heterogeneous mixture was cooled to 0° C. and 20 ml. of a solution containing 4.1 g of sodium nitrite was added so that the temperature did not exceed 5° C. The resulting reaction mixture was allowed to come to room temperature by stirring overnight. Stirring was continued for a total of 2 days at room temperature. A flocculent light yellow precipitate was obtained. The light yellow solid was collected by filtration, washed with water and then dried by dissolving in methylene chloride and storing over anhydrous magnesium sulfate. The stored solution was filtered and concentrated to yield [N-(cyanomethyl)-N-nitrosoamino]methylphosphonic acid, bis(2-methoxyphenyl) ester, having a melting point of 83°–85° C. and giving the following analysis:
Calculated: C, 52.18; H, 4.64; N, 10.74.
Found: C, 52.14; H, 4.66; N, 10.74.

EXAMPLE 4

Bis(4-methoxyphenoxy)phosphinylmethylglycinonitrile methyl sulfonic acid salt (9.16 g, 0.02 mole) and 15 ml. of 10-normal hydrochloric acid were combined in 150 ml. of water, cooled and an aqueous solution containing 4.14 g (0.06 mole) of sodium nitrite was added dropwise so that the temperature did not rise above 5° C. The resulting reaction mixture was stirred at 5° C. for 30 minutes and then at room temperature for 2 days. The aqueous layer was decanted and the residue washed with voluminous quantities of distilled water. The residue was then dissolved in methylene chloride, dried over magnesium sulfate, filtered and concentrated to yield [N-(cyanomethyl)-N-nitrosoamino]methylphosphonic acid, bis(4-methoxyphenyl) ester, as a yellow oil and having the following analysis:

Calculated: C, 52.18; H, 4.64; N, 10.74.
Found: C, 52.20; H, 4.67; N, 10.75.

EXAMPLE 5

Dihydroxyphosphinylmethylglycinonitrile (2.0 g, 0.0133 mole) was dissolved in 20 ml. of water, cooled to 0°–5° C. and 10 ml. of approximately 10-normal hydrochloric acid added. The resulting mixture was stirred and then a solution of sodium nitrite (1.04 g, 0.0150 mole) dissolved in 10 g of water was added dropwise over a 45-minute period. At the end of the addition, all the solids had dissolved and a red-brown faint color was present. The reaction mixture was stirred for 1 hour in an ice bath during which time the color faded. The mixture was stirred for 3 hours at room temperature and subjected to medium pressure ion exchange chromatography. The cuts 10–15 were boiled down by rotoevaporation. The samples were redissolved in water, decanted and again concentrated, dried over potassium hydroxide pellets in a dessicator at less than 1 mm. pressure to yield 2.46 g of a light tan flexible glass identified as N-nitroso-N-phosphonomethylaminoacetonitrile, monohydrate, having the following analysis:

Calculated: C, 18.28; H, 4.09; N, 21.32; P, 15.72.
Found: C, 17.56; H, 3.60; N, 20.72; P, 15.32.

EXAMPLE 6

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical. In that 6 ml is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
| --- | --- |
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:
A—Canada Thistle*
B—Cocklebur
C—Velvetleaf
D—Morningglory
E—Lambsquarters
F—Smartweed
G—Yellow Nutsedge*
H—Quackgrass*
I—Johnsongrass*
J—Downy Brome
K—Barnyardgrass
L—Soybean
M—Sugar Beet
N—Wheat
O—Rice
P—Sorghum
Q—Wild Buckwheat
R—Hemp Sesbania
S—Panicum Spp
T—Crabgrass

*—Established from vegetative propagules.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 4 | 11.2 | 2 | 3 | 3 | 3 | 4 | 2 | 1 | 2 | 1 | 1 | 3 |
| 1 | 4 | 5.6 | 1 | 3 | 2 | 2 | 4 | 1 | 2 | 0 | 2 | 2 | 2 |
| 2 | 4 | 11.2 | 1 | 2 | 1 | 1 | — | 4 | 2 | 1 | 2 | 1 | 2 |
| 2 | 4 | 5.6 | 1 | 1 | 1 | 1 | 4 | 2 | 2 | 0 | 2 | 1 | 2 |
| 3 | 4 | 11.2 | 0 | 2 | 0 | 1 | 3 | 1 | 0 | 0 | 0 | 0 | 2 |
| 4 | 4 | 11.2 | 0 | 3 | 1 | 1 | 1 | 0 | 0 | 1 | 1 | 0 | 2 |
| 4 | 4 | 5.6 | 1 | 3 | 2 | 1 | 1 | 0 | 1 | 1 | 0 | 0 | 1 |

TABLE I-continued

| Compound of Example No. | WAT | kg/h | A | B | C | D | E | F | G | H | I | J | K |
|---|---|---|---|---|---|---|---|---|---|---|---|---|---|
| 5 | 4 | 11.2 | 0 | 2 | 1 | 1 | 1 | 3 | 0 | 0 | 0 | 0 | 1 |
| 5 | 2 | 5.6 | 0 | 0 | 1 | 1 | 1 | 0 | 0 | 0 | 0 | 0 | 0 |

TABLE II

| Compound of Example No. | WAT | kg/ha | L | M | N | O | P | B | Q | D | R | E | F | C | J | S | K | T |
|---|---|---|---|---|---|---|---|---|---|---|---|---|---|---|---|---|---|---|
| 1 | 4 | 5.6 | 2 | 1 | 1 | 3 | 3 | 2 | 2 | 2 | 2 | 4 | 4 | 3 | 3 | 3 | 3 | 3 |
| 1 | 4 | 1.12 | 0 | 0 | 0 | 1 | 3 | 1 | 1 | 2 | 3 | 2 | 2 | 3 | 2 | 1 | 2 | 3 |
| 1 | 4 | 0.28 | 0 | 0 | 0 | 0 | 1 | 0 | 0 | 1 | 0 | 1 | 0 | 0 | 1 | 1 | 1 | 1 |
| 2 | 4 | 5.6 | 1 | 1 | 2 | 1 | 3 | 3 | 2 | 2 | 2 | 2 | 2 | 2 | 2 | 3 | 3 | 2 |
| 2 | 4 | 1.12 | 0 | 0 | 1 | 0 | 2 | 2 | 2 | 2 | 1 | — | 1 | 1 | 1 | 0 | 2 | 3 |
| 2 | 2 | 0.28 | 0 | 0 | 0 | 0 | 1 | 2 | 1 | 1 | 1 | — | 1 | 0 | 1 | 0 | 1 | 2 |
| 4 | 4 | 5.6 | 1 | 4 | 2 | 2 | 3 | 4 | 2 | 3 | 4 | 4 | 4 | 2 | 3 | 2 | 3 | 3 |
| 4 | 2 | 1.12 | 0 | 0 | 0 | 0 | 1 | 1 | 0 | 0 | 0 | 0 | 0 | 1 | 0 | 0 | 1 | 1 |
| 5 | 4 | 5.6 | 1 | 0 | 1 | 0 | 0 | 1 | 1 | 1 | — | 2 | 1 | 1 | 0 | 1 | 0 | 1 |
| 5 | 2 | 1.12 | 1 | 1 | 0 | 0 | 0 | 0 | 0 | — | 0 | 1 | 1 | 0 | 0 | 0 | 2 | 1 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids aand soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

| | |
|---|---|
| 1. (N-nitroso-N-cyanomethylamino)methylphosphonic acid, diphenyl ester | 95 parts |
| Methanol | 5 parts |
| 2. (N-nitroso-N-cyanomethylamino)methylphosphonic acid, di(4-chloro-3-methylphenyl) ester | 95 parts |
| Ethoxylated nonyl phenol | 5 parts |
| 3. (N-nitroso-N-cyanomethylamino)methylphosphonic acid, bis(2-methoxyphenyl) ester | 90 parts |
| Isopropanol | 10 parts |
| 4. (N-(cyanomethyl)-N-nitrosoamino)-methylphosphonic acid, bis(4-methoxyphenyl) ester | 90 parts |
| Ethoxylated octyl phenol | 10 parts |
| 5. N-nitroso-N-phosphonomethylaminoacetonitrile monohydrate | 90 parts |
| Chloroform | 5 parts |
| Ethoxylated dinonyl phenol | 5 parts |
| 6. (N-nitroso-N-cyanomethylamino)methylphosphonic acid, diphenyl ester | 75 parts |
| Butanol | 25 parts |
| 7. (N-nitroso-N-cyanomethylamino)-methylphosphonic acid, di(4-chloro-3-methylphenyl) ester | 75 parts |
| Ethoxylated oleyl alcohol | 25 parts |
| 8. (N-nitroso-N-cyanomethylamino)methylphosphonic acid, bis(2-methoxyphenyl) ester | 75 parts |
| Acetonitrile | 15 parts |
| Ethoxylated cocoamine | 10 parts |
| 9. (N-(cyanomethyl)-N-nitrosoamino)-methylphosphonic acid, bis(4-methoxyphenyl) ester | 75 parts |
| 1,2-Dimethoxyethane | 20 parts |
| Ethoxylated tallow amine | 5 parts |

| | | |
|---|---|---|
| 10. N-nitroso-N-phosphonomethylamino-acetonitrile monohydrate | 50 parts | |
| Dimethylformamide | 50 parts | |
| 11. (N-nitroso-N-cyanomethylamino)-methylphosphonic acid, diphenyl ester | 50 parts | |
| Isopropyl dodecylbenzene sulfonate | 50 parts | |
| 12. (N-nitroso-N-cyanomethylamino)-methylphosphonic acid, di(4-chloro-3-methylphenyl) ester | 50 parts | |
| Dimethylsulfoxide | 40 parts | |
| Ethoxylated soybeanamine | 10 parts | |
| 13. (N-nitroso-N-cyanomethylamino)-methylphosphonic acid, bis(2-methoxyphenyl) ester | 50 parts | |
| γ-butyrolactone | 25 parts | |
| Triethanolamine dodecylbenzene sulfonate | 25 parts | |
| 14. (N-(cyanomethyl)-N-nitrosoamino)-methylphosphonic acid, bis(4-methoxyphenyl) ester | 50 parts | |
| 1,1,1-Trichloroethane | 42 parts | |
| Ethoxylated nonyl phenol | 8 parts | |
| 15. N-nitroso-N-phosphonomethylamino-acetonitrile monohydrate | 25 parts | |
| Chloroform | 75 parts | |
| 16. (N-nitroso-N-cyanomethylamino)-methylphosphonic acid, diphenyl ester | 25 parts | |
| Chloroform | 70 parts | |
| Ethoxylated tallow amine | 5 parts | |
| 17. (N-nitroso-N-cyanomethylamino)-methylphosphonic acid, di(4-chloro-3-methylphenyl) ester | 25 parts | |
| 1,1,1-Trichloroethane | 74 parts | |
| Ethoxylated oleyl alcohol | 1 part | |
| 18. (N-nitroso-N-cyanomethylamino)-methylphosphonic acid, bis(2-methoxyphenyl) ester | 25 parts | |
| Chloroform | 68 parts | |
| Ethoxylated dinonyl phenol | 7 parts | |
| 19. (N-(cyanomethyl)-N-nitrosoamino)-methylphosphonic acid, bis(4-methoxyphenyl) ester | 10 parts | |
| Chloroform | 90 parts | |
| 20. N-nitroso-N-phosphonomethylamino)-acetonitrile monohydrate | 10 parts | |
| Methanol | 80 parts | |
| Polyoxypropylene - polyoxyethylene block copolymer | 10 parts | |
| 21. (N-nitroso-N-cyanomethylamino)-methylphosphonic acid, diphenyl ester | 10 parts | |
| Ethanol | 88 parts | |
| Polyoxyethylene (20) sorbitan-monolaurate | 2 parts | |
| 22. (N-nitroso-N-cyanomethylamino)-methylphosphonic acid, di(4-chloro-3-methylphenyl) ester | 10 parts | |
| Isopropanol | 72 parts | |
| Polyoxyethylene sorbitan-monooleate | 18 parts | |
| 23. (N-nitroso-N-cyanomethylamino)-methylphosphonic acid, bis(2-methoxyphenyl) ester | 5 parts | |
| Dimethylformamide | 95 parts | |
| 24. (N-(cyanomethyl)-N-nitrosoamino)-methylphosphonic acid, bis(4-methoxyphenyl) ester | 5 parts | |
| Acetonitrile | 90 parts | |
| Ethoxylated tallow amine | 5 parts | |
| 25. N-nitroso-N-phosphonomethylamino-acetonitrile monohydrate | 5 parts | |
| Ethanol | 94 parts | |
| Ethoxylated tallow amine | 1 part | |
| 26. (N-nitroso-N-cyanomethylamino)-methylphosphonic acid, di(4-chloro-3-methylphenyl) ester | 5 parts | |
| Isopropanol | 80 parts | |
| Ethoxylated cocoamine | 15 parts | |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. An effective amount for phytotoxic or herbicidal control is that amount necessary for overall or selective control, i.e., a phytotoxic or herbicidal amount. It is believed that one skilled in the art can readily determined from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

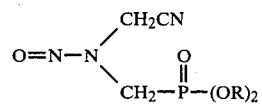

wherein R is a member of the group consisting of hydrogen, phenyl and phenyl substituted with from 1 to 2 substituents selected from the class consisting of halogen, lower alkyl and lower alkoxy.

2. A compound of claim 1 wherein R is hydrogen.

3. A compound of claim 1 wherein R is phenyl.

4. A compound of claim 1 wherein R is phenyl substituted with from 1 to 2 substituents selected from the class consisting of halogen, lower alkyl and lower alkoxy.

5. A compound of claim 4 which is N-nitroso-N-(cyanomethylamino)methylphosphonic acid, di(4-chloro-3-methylphenyl) ester.

6. A compound of claim 4 which is N-nitroso-N-(cyanomethylamino)methylpyosphonic acid, di(2-methoxyphenyl) ester.

7. A composition comprising a herbicidally effective amount of a compound of claim 1 and a herbicidally acceptable adjuvant.

8. A composition comprising a herbicidally effective amount of a compound of claim 2 and a herbicidally acceptable adjuvant.

9. A composition comprising a herbicidally effective amount of a compound of claim 3 and a herbicidally acceptable adjuvant.

10. A composition comprising a herbicidally effective amount of a compound of claim 4 and a herbicidally acceptable adjuvant.

11. A composition comprising a herbicidally effective amount of a compound of claim 5 and a herbicidally acceptable adjuvant.

12. A composition comprising a herbicidally effective amount of a compound of claim 6 and a herbicidally acceptable adjuvant.

13. A herbicidal method which comprises contacting a plant with a herbicidally effective amount of a compound of claim 1.

14. A herbicidal method which comprises contacting a plant with a herbicidally effective amount of a compound of claim 2.

15. A herbicidal method which comprises contacting a plant with a herbicidally effective amount of a compound of claim 3.

16. A herbicidal method which comprises contacting a plant with a herbicidally effective amount of a compound of claim 4.

17. A herbicidal method which comprises contacting a plant with a herbicidally effective amount of a compound of claim 5.

18. A herbicidal method which comprises contacting a plant with a herbicidally effective amount of a compound of claim 6.

* * * * *